(12) United States Patent
Goerz et al.

(10) Patent No.: US 11,806,173 B2
(45) Date of Patent: Nov. 7, 2023

(54) STACKING DEVICE FOR MESH STERILIZING TRAYS

(71) Applicant: Aesculap AG, Tuttlingen (DE)

(72) Inventors: Dennis Goerz, Tuttlingen (DE); Bianca Rosin, Tuttlingen (DE); Eva Streit, Bodman-Ludwigshafen (DE); Timo Knittel, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 214 days.

(21) Appl. No.: 17/432,718

(22) PCT Filed: Feb. 20, 2020

(86) PCT No.: PCT/EP2020/054562
§ 371 (c)(1),
(2) Date: Aug. 20, 2021

(87) PCT Pub. No.: WO2020/169778
PCT Pub. Date: Aug. 27, 2020

(65) Prior Publication Data
US 2022/0054216 A1 Feb. 24, 2022

(30) Foreign Application Priority Data
Feb. 22, 2019 (DE) ............. 10 2019 104 599.1

(51) Int. Cl.
*A61B 50/33* (2016.01)
*A61B 50/00* (2016.01)
*A61B 50/30* (2016.01)

(52) U.S. Cl.
CPC ........ *A61B 50/33* (2016.02); *A61B 2050/006* (2016.02); *A61B 2050/0075* (2016.02); *A61B 2050/3007* (2016.02)

(58) Field of Classification Search
CPC ............. A61B 50/33; A61B 2050/006; A61B 2050/0075; A61B 2050/3007
(Continued)

(56) References Cited

U.S. PATENT DOCUMENTS 4,541,992 A * 9/1985 Jerge ..................... A61B 50/31
422/310
4,730,729 A * 3/1988 Monch ................... A61B 50/30
206/370

(Continued)

FOREIGN PATENT DOCUMENTS

DE 7439414 U 4/1975
DE 3413386 A1 10/1985
(Continued)

OTHER PUBLICATIONS

Written Opinion received in International Application No. PCT/EP2020/054562 dated May 29, 2020, with translation, 11 pages.
(Continued)

*Primary Examiner* — Jacob K Ackun
(74) *Attorney, Agent, or Firm* — Christopher A. Rothe; Culhane Meadows PLLC

(57) ABSTRACT

A stackable sieve tray for receiving medical products, preferably for sterilization, has a sieve tray bottom and upward-extending sieve tray sidewalls arranged at the sieve tray bottom. The sieve tray bottom, on its underside, has an indentation in edge regions that holds at least two sieve trays in position with respect to each other in a length and width direction of the sieve trays when the sieve trays are stacked, the indentation of a first sieve tray engaging the sieve tray sidewalls of a second sieve tray.

4 Claims, 4 Drawing Sheets

(58) Field of Classification Search
USPC .................................................. 206/370
See application file for complete search history.

(56) References Cited

U.S. PATENT DOCUMENTS

| | | | | |
|---|---|---|---|---|
| 5,065,885 | A | | 11/1991 | Scaroni |
| 5,424,048 | A | | 6/1995 | Riley |
| 5,540,901 | A | * | 7/1996 | Riley ..................... A61B 50/22 |
| | | | | 206/370 |
| 6,012,577 | A | | 1/2000 | Ewis et al. |
| 6,116,452 | A | * | 9/2000 | Hamel .................. B65D 45/20 |
| | | | | 220/345.2 |
| 6,152,318 | A | * | 11/2000 | Walker .................. B65D 55/16 |
| | | | | 206/508 |
| 6,350,418 | B1 | * | 2/2002 | Venderpool ............ B65D 55/12 |
| | | | | 292/37 |
| 8,544,648 | B2 | * | 10/2013 | Cleveland .............. B65D 45/22 |
| | | | | 220/592.2 |
| 8,668,111 | B2 | | 3/2014 | Orr |
| 11,071,605 | B2 | | 7/2021 | Goerz et al. |
| 2003/0118491 | A1 | * | 6/2003 | Frieze ...................... A61L 2/26 |
| | | | | 422/292 |
| 2004/0129595 | A1 | * | 7/2004 | Dane ....................... A61L 2/26 |
| | | | | 206/370 |
| 2004/0144670 | A1 | * | 7/2004 | Riley ..................... A61B 50/30 |
| | | | | 206/439 |
| 2005/0158222 | A1 | * | 7/2005 | Bettenhausen ........... A61L 2/26 |
| | | | | 29/592 |
| 2006/0144743 | A1 | * | 7/2006 | McDade ............ B65D 21/0235 |
| | | | | 206/503 |
| 2007/0205123 | A1 | | 9/2007 | Bettenhausen et al. |
| 2007/0212277 | A1 | | 9/2007 | Riley |
| 2007/0215507 | A1 | * | 9/2007 | Glenn .................... A61B 50/33 |
| | | | | 206/557 |
| 2008/0116098 | A1 | * | 5/2008 | Marooflan ........... B65D 77/225 |
| | | | | 206/503 |
| 2009/0146032 | A1 | * | 6/2009 | Bettenhausen ........ A61B 50/30 |
| | | | | 248/220.31 |
| 2011/0155613 | A1 | * | 6/2011 | Koenig .............. B65D 21/0223 |
| | | | | 206/503 |
| 2012/0195792 | A1 | * | 8/2012 | Duddy ...................... A61L 2/26 |
| | | | | 422/28 |
| 2013/0105346 | A1 | * | 5/2013 | Ramkhelawan ....... A61B 50/33 |
| | | | | 206/370 |
| 2013/0108503 | A1 | * | 5/2013 | Ramkhelawan ....... A61B 50/34 |
| | | | | 422/1 |
| 2014/0077435 | A1 | * | 3/2014 | Powell .................. A61B 50/34 |
| | | | | 269/308 |
| 2014/0216966 | A1 | * | 8/2014 | Ramkhelawan ....... A61B 50/30 |
| | | | | 206/370 |
| 2014/0339114 | A1 | * | 11/2014 | Griffin .................. A61B 50/20 |
| | | | | 206/370 |
| 2016/0151526 | A1 | * | 6/2016 | Roudebush ............... A61L 2/26 |
| | | | | 422/310 |
| 2017/0224434 | A1 | * | 8/2017 | Schwartzbauer ...... A61B 50/33 |
| 2018/0028703 | A1 | * | 2/2018 | McLaughlin .......... A61B 50/34 |
| 2018/0221525 | A1 | * | 8/2018 | Houde ................... A61B 50/33 |
| 2019/0201571 | A1 | * | 7/2019 | Lucier ....................... A61L 2/26 |
| 2021/0259797 | A1 | * | 8/2021 | Görz ......................... A61L 2/26 |
| 2022/0054216 | A1 | * | 2/2022 | Goerz .................... A61B 50/33 |
| 2022/0125543 | A1 | * | 4/2022 | Birkbeck ............... A61B 50/34 |
| 2022/0175999 | A1 | * | 6/2022 | Klemm .................. A61B 50/22 |
| 2022/0370166 | A1 | * | 11/2022 | Goerz .................... A61B 50/34 |

FOREIGN PATENT DOCUMENTS

| | | |
|---|---|---|
| DE | 20105328 U1 | 7/2001 |
| DE | 102010050919 A1 | 5/2012 |
| DE | 102012003983 A1 | 8/2013 |
| DE | 102012016970 A1 | 3/2014 |
| DE | 102018104942 A1 | 9/2019 |
| DE | 102018130542 A1 | 1/2020 |
| EP | 3434611 A2 | 1/2019 |
| WO | 2004089774 A1 | 10/2004 |
| WO | 2019197494 A1 | 10/2019 |
| WO | 2020169778 A1 | 8/2020 |

OTHER PUBLICATIONS

Search Report received in German Application No. 10 2019 104 599.1 dated Oct. 31, 2019, with translation, 10 pages.
Search Report received in International Application No. PCT/EP2020/054562 dated May 29, 2020, with translation, 6 pages.
Ermis, Perforated sheet screen baskets, Stainless Steel Screen Baskets, www.ermis-medizintechnik.de, 2018, 1 page.
Search Report received in German Application No. 10 2019 129 061.9 dated Jun. 29, 2020, with translation, 10 pages.
Search Report received in International Application No. PCT/EP2020/080009 dated Feb. 5, 2021, with translation, 7 pages.
Written Opinion received in International Application No. PCT/EP2020/080009 dated Feb. 5, 2021, with translation, 17 pages.

* cited by examiner

STACKING DEVICE FOR MESH STERILIZING TRAYS

CROSS-REFERENCE TO RELATED APPLICATIONS

This application is the United States national phase entry of International Application No. PCT/EP2020/054562, filed Feb. 20, 2020, and claims the benefit of priority of German Application No. 10 2019 104 599.1, filed Feb. 22, 2019. The contents of International Application No. PCT/EP2020/054562 and German Application No. 10 2019 104 599.1 are incorporated by reference herein in their entireties.

FIELD

The present disclosure relates to a stackable sieve tray for holding medical products, in particular for sterilization or insertion into a sterile container.

BACKGROUND

It is known that sterilization sieve trays have to be stored for transport in a processing unit for medical products or for sterilization in sterile barrier systems. In order to use as little storage space as possible, it is necessary to be able to stack these sieve trays in a way that is as space-saving and safe as possible.

For example, sterilization sieve trays are known which require an additional element for the stacking function. The additional element has to be attached to the sterilization sieve tray, for example via a clamping device. In DE 10 2012 016 970 A1, a sieve tray is disclosed which can be connected to at least one second sieve tray via flat clamping springs or clamping clips. The clamping clips face inwards and are engaged at openings formed in the sieve tray walls. Alternatively, sterilization sieve trays are also known, in which the stacked sieve trays are each supported against each other by sieve tray feet. If soft packaging is used as the sterile barrier system, it may be damaged due to the point load caused by the sieve tray feet. If the stackable sterilization sieve trays known to date are additionally closed with a lid and stacked with the lid, there is no lateral stop, which easily causes the upper, stacked sieve tray to slip.

SUMMARY

The object of the present invention is therefore to provide a sieve tray which allows safe stacking of sieve trays with and without a sieve tray lid.

The (stackable) sieve tray according to the invention for holding medical products, preferably for sterilization, has a sieve tray bottom and sieve tray sidewalls arranged on the sieve tray bottom and extending essentially perpendicularly thereto. A circumferential indentation is formed/arranged on an outer/lower side of the sieve tray bottom in its edge regions, said indentation fixing at least two sieve trays to each other in a stacked state in a length and width direction of the sieve tray. For this purpose, the circumferential indentation of a first upper sieve tray engages with the sieve tray sidewalls of a second lower sieve tray. This configuration of the sieve tray makes it possible to stack several sieve trays securely on top of each other without having to provide additional components on the sieve trays.

According to the invention, the stackable sieve tray may be configured such that a depth of the circumferential indentation substantially corresponds to a thickness of the sieve tray sidewall. Thus, if outer surfaces of stacked sieve trays have substantially flush surfaces with each other, this reduces the space required for stacked sieve trays and facilitates handling of a stack of trays. It is also advantageous if the circumferential indentation is essentially conical. I.e. the circumferential indentation extends outwards from the sieve tray bottom and tapers so that the inner cross-sectional area defined by the circumferential indentation decreases in the direction in which the circumferential indentation extends. The conicity of the circumferential indentation also facilitates the stacking of two sieve trays, as the indentation acts as an additional guide during stacking and the stacked sieve trays are also centered relative to each other.

In one embodiment according to the invention, the stackable sieve tray furthermore has at least one grip handle which is rotatably articulated to a sieve tray sidewall and a sieve tray lid closing the sieve tray. On the sieve tray lid, a substantially circumferential indentation is formed which is intermitted/interrupted in a region of the grip handle and which fixes at least two sieve trays, of which at least one sieve tray, preferably the lower sieve tray, is closed by the sieve tray lid, to each other in the stacked state, in that the indentation of the sieve tray lid engages with the indentation of the upper sieve tray. The sieve tray lid also has a circumferential, projecting rim on its outer side, which is intermitted in the region of the grip handle and encloses an upper edge of the sieve tray sidewalls when the sieve tray lid is placed on the sieve tray. This has the advantage that even when using a sieve tray with sieve tray lid, safe stacking is ensured and possible slipping of the sieve trays relative to each other can be prevented. Slipping of the sieve tray lid on the sieve tray can also be prevented with the sieve tray sidewalls being gripped by the projecting rim of the sieve tray lid.

In one embodiment according to the invention, the sieve tray lid is recessed downwards in the region of the grip handle, i.e. pressed inwards in the shape of a trough, so that the grip handle can sink into the trough in a folded-in position and thus is essentially flush with the surface of the sieve tray lid, which enables the sieve trays with grip handles hinged thereto to be stacked securely on top of each other without having to make any complicated changes to the sieve tray.

A grip handle depression is formed centrally on the receiving portion of the grip handle in the sieve tray lid, which is recessed downwards/inwards. The grip handle depression improves handling of the sieve tray, since the grip handle can be easily grasped in the folded-in state even when the sieve tray lid is placed on top.

BRIEF DESCRIPTION OF THE DRAWING FIGURES

DETAILED DESCRIPTION

The following is a description of a configuration example of the present disclosure based on the accompanying figures.

Figure 1:
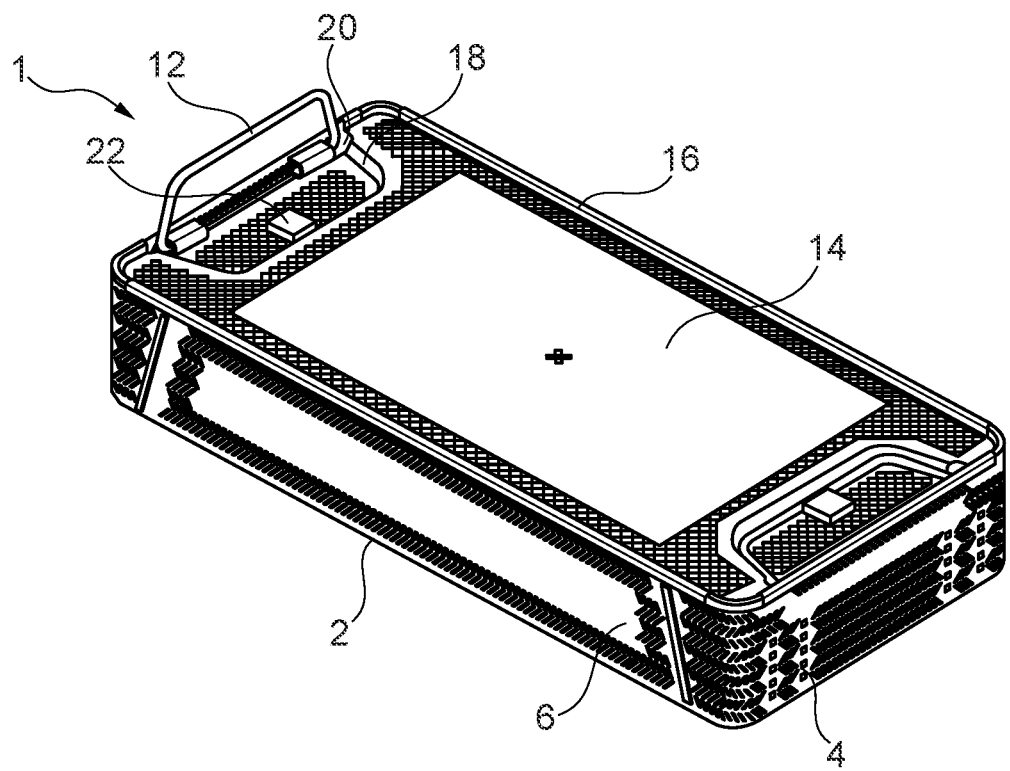
FIG. 1 is a perspective view of a stackable sieve tray according to a preferred configuration example.

FIG. 1 is a perspective view of a stackable sieve tray 1 according to a preferred configuration example. The sieve tray 1 has a substantially rectangular sieve tray bottom 2 and sieve tray sidewalls 4, 6 arranged on the sieve tray bottom 2 and extending upwards.

The sieve tray bottom 2 is made from a (perforated) metal plate in which a large number of through-holes 10 are punched side by side, wherein the material of the sieve tray bottom 2 remains between the through-holes 10 in the form of narrow crosspieces 9. In the preferred configuration example, the through-holes 10 are elongated holes with rounded corners, but may also have a square or rectangular cross-section. Analogous to the sieve tray bottom 2, the sieve tray sidewalls 4, 6 are also configured with elongated through-holes 10 and crosspieces 9 remaining in between.

Alternatively, the sieve tray bottom 2 and the sieve tray sidewalls 4, 6 may also have any other shape. For example, it is possible to configure them without through-holes 10 or to build them from a grid-like or net-like structure, which is created by interweaving a plurality of metal wires running parallel to each other with a plurality of metal wires also running parallel to each other and perpendicular to the first metal wires in such a way that square or rectangular through-holes are created between the metal wires.

On two opposite sieve tray sidewalls 4, preferably the two sieve tray sidewalls 4, which are arranged on short sides of the rectangular sieve tray bottom 2, a grip handle 12 is articulated centrally at an upper end/end portion in a rotatable manner. According to the preferred configuration example, the grip handle 12 is arranged on the sieve tray sidewall 4 in such a way that, in a folded-in state, it projects substantially perpendicularly to the sieve tray sidewall 4 towards an inner side of the sieve tray 1. In an unfolded state, the grip handle 12 extends upwards substantially parallel to the sieve tray sidewall 4.

Figure 2:
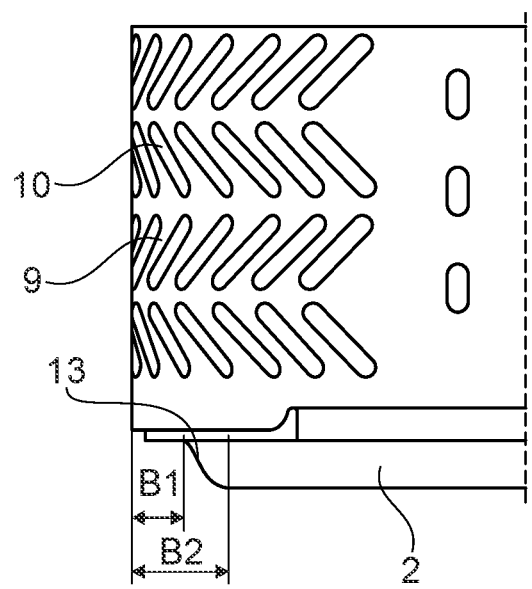
FIG. 2 is a side view of a section of the stackable sieve tray according to the preferred configuration example.
Figure 3:
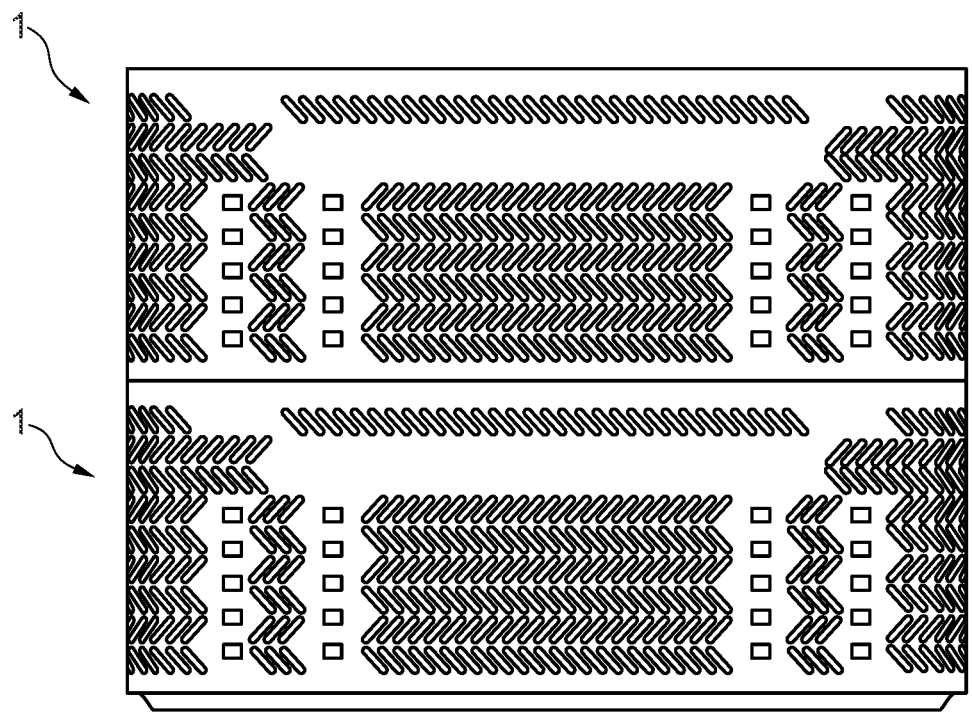
FIG. 3 is a side view of two stackable sieve trays according to the preferred configuration example.

FIG. 2 is a side view of a section of the stackable sieve tray 1 according to the preferred configuration example. In edge regions of the sieve tray bottom 2, a circumferential indentation/frame-shaped recess 13 is formed on its underside, which recesses the sieve tray bottom 2 towards its center. A width B1 of the indentation/recess 13 in the region of the sieve tray bottom 2 corresponds substantially to a thickness of the sieve tray sidewalls 4, 6, so that, as shown in FIG. 3, stacked sieve trays 1 according to the preferred configuration example can be fixed to each other in a length direction and width direction of the sieve tray 1 in that the indentation 13 of the upper sieve tray 1 engages with the sieve tray sidewalls 4, 6 of the lower sieve tray 1.

In addition, as can be seen in FIG. 2, the indentation 13 is conical in the preferred configuration example. I.e. in its direction of extension (downwards in FIG. 2) an inner cross-sectional area defined by the indentation 13 decreases. A width B2 at an end section of the indentation 13 facing away from the sieve tray base 2 is thus larger than the width B1.

In FIG. 2, it can also be seen that the indentation 13 essentially follows the shape of an arc cotangent in a lateral view. I.e. the indentation 13 has a first radius with a concave curvature in the region of the sieve tray bottom 2 and a second radius with a convex curvature at the end portion of the indentation 13 facing away from the sieve tray bottom 2.

In other words, when at least two sieve trays 1 are stacked on top of each other according to the preferred configuration example, the indentation 13 of the sieve tray bottom 2 of the upper sieve tray 1 is supported by the sieve tray sidewalls 4, 6 of the lower sieve tray 1 such that slipping of the two sieve trays 1 relative to each other can be prevented in the stacked state. Furthermore, according to the preferred configuration example, the sieve trays 1 are configured such that the sieve tray sidewalls 4, 6 of the lower and upper sieve trays 1 have substantially flush surfaces with each other in the stacked state, as shown in FIG. 3.

In still other words, the sieve tray bottom 2 is preferably provided with a frame-shaped circumferential recess 13 by press molding, resulting in a kind of bottom projection/bottom extension which can be pressed into another, preferably identically constructed, sieve tray with a substantially accurate fit/with little play, thus coupling both sieve trays together in the manner of play blocks of known design.

Figure 4:
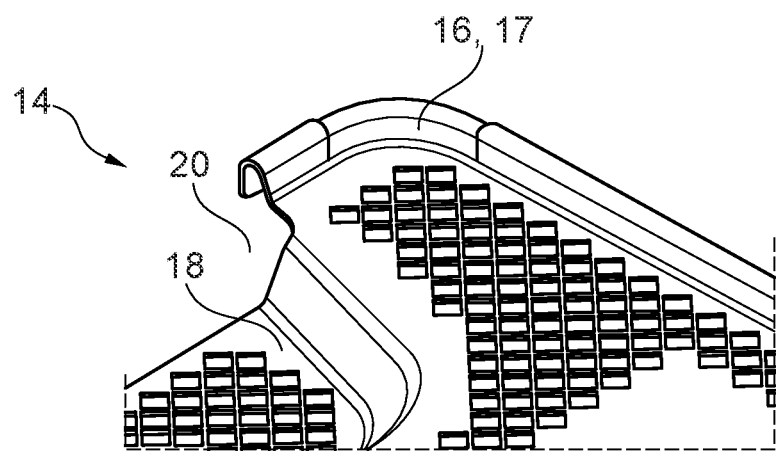
FIG. 4 is a section of a sieve tray lid of a stackable sieve tray according to the preferred configuration example.

FIG. 4 shows a section of a sieve tray lid 14 for closing a stackable sieve tray 1 according to the preferred configuration example. The sieve tray lid 14 has a substantially rectangular shape, analogous to the sieve tray 1, at the rim regions of which a circumferential rim/frame/bead 16 is formed projecting onto an outer side. The rim 16 projecting upwards is substantially formed in an arc/bead/strip shape. A width of the projecting rim 16 corresponds to the thickness of the sieve tray sidewalls 4, 6, so that when the sieve tray lid 14 is placed on the sieve tray 1, the projecting rim 16 engages around the sieve tray sidewalls 4, 6 on both sides (inside and outside) and fixes the sieve tray lid 14 to the sieve tray 1 in the length and width direction of the sieve tray 1.

In other words, the projecting rim 16 of the sieve tray lid 14 engages around the sieve tray sidewalls 4, 6 in a groove or spring-like manner when the sieve tray 1 is closed with the sieve tray lid 14 so that the sieve tray 1 and the sieve tray lid 14 are prevented from slipping relative to each other.

Analogous to the sieve tray 1, the sieve tray lid 14 is made of a metal plate in which a large number of through-holes 10 are punched side by side, wherein the material of the sieve tray lid 14 remains between the through-holes 10 in the form of narrow crosspieces 9. In the preferred configuration example, the through-holes 10 are configured as elongated holes with rounded corners, but may also have a square or rectangular cross-section.

Alternatively, the sieve tray lid 14 may also have any other shape. For example, it is possible to configure it without through-holes 10 or only partially with through-holes 10 or to build it from a net-like structure, which is created by interweaving a plurality of metal wires running parallel to each other with a plurality of metal wires also running parallel to each other and perpendicular to the first metal wires in such a way that square or rectangular through-holes are created between the metal wires.

In FIG. 1 and FIG. 4, it can be seen that the sieve tray lid 14 is not formed with through-holes 10 over its entire surface. A central surface of the sieve tray lid 14 is configured here as a closed surface. However, this central surface is shown as a closed surface without through-holes only for clarity, and the sieve tray lid 14 is configured with through-holes 10 over its entire surface in the preferred configuration example as described above.

As can be seen in FIG. 4, a circumferential indentation/sink 17 is also formed on the sieve tray lid 14, which results from the rim 16 projecting upwards in a frame shape with respect to the central surface of the sieve tray lid 14 and substantially corresponds to the cross-section of the bottom extension. Thus, it is possible to stack at least two sieve trays 1 on top of each other, even when the lower sieve tray 1 is closed with the sieve tray lid 14, since in this case the indentation (bottom extension) 13 on the sieve tray bottom 2 of the upper sieve tray 1 engages with the indentation/sink 17 of the sieve tray lid 14. As a result, lateral slippage of the lower sieve tray 1 including the sieve tray lid 14 and the upper sieve tray 1 relative to each other can be prevented, as described above.

In addition, centrally on the short sides of the sieve tray lid 14, a portion of the sieve tray lid 14 is recessed downwards over another indentation in a trough-like manner so that when the sieve tray lid 14 is placed on the sieve tray 1 and the grip handle 12 is in the folded state, the grip handle 12 is recessed substantially flush with the surface in a grip handle-receiving portion (grip recess) 18 formed by recessing of the sieve tray lid 14 and does not project beyond the sieve tray lid 14. Preferably, the depth of the grip handle-receiving portion 18 substantially corresponds to a thickness of the grip handle 12.

Furthermore, in order to easily place the sieve tray lid 14 on the sieve tray 1, a grip handle recess 20 is formed in an area of the grip handle-receiving portion 18 near the sieve tray sidewall. A width of the grip handle recess 20 substantially corresponds to a depth of the articulation of the grip handle 12, so that when the sieve tray lid 14 is placed on the sieve tray 1, the grip handle 12 simply slides through the grip handle recess 20 and is subsequently foldable.

In order to prevent unintentional lifting of the sieve tray lid 14 from the sieve tray 1, a grip-handle closing element 22 is arranged centrally on a respective edge region of the grip handle-receiving portion 18 arranged in the direction of the center of the sieve tray lid 14. In the preferred configuration example, this grip-handle closing element 22 has a recess which receives and holds the grip handle 12 in the folded state and thus fixes the sieve tray lid 14 to the sieve tray 1. Alternatively, the grip-handle closing element 22 may also be configured such that the grip handle 12 is clamped and thus fixed between the grip-handle closing element 22 and a wall of the grip handle-receiving portions 18 in the folded state.

In addition, the sieve tray lid 14 may be gripped and lifted via the grip-handle closing elements 22 in the unfolded state of the grip handle 12. This additionally improves handling of the sieve tray 1 and the sieve tray lid 14.

Figure 5:
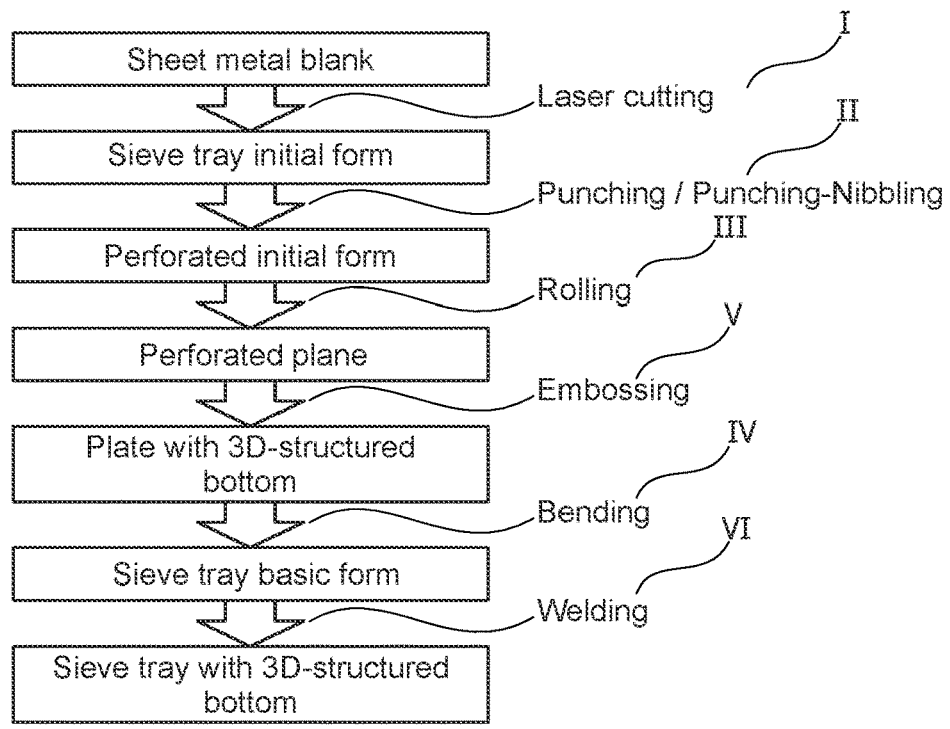
FIG. 5 is a flow chart of a method for manufacturing the stackable sieve tray.

FIG. 5 chronologically shows a first possibility of a process sequence for the manufacturing of the sieve tray 1. Thereby, laser cutting I, punching II (also punching-nibbling, if the part to be punched out is only partially punched and partially broken), rolling III, embossing V, bending IV and welding VI take place chronologically one after the other.

Figure 6:
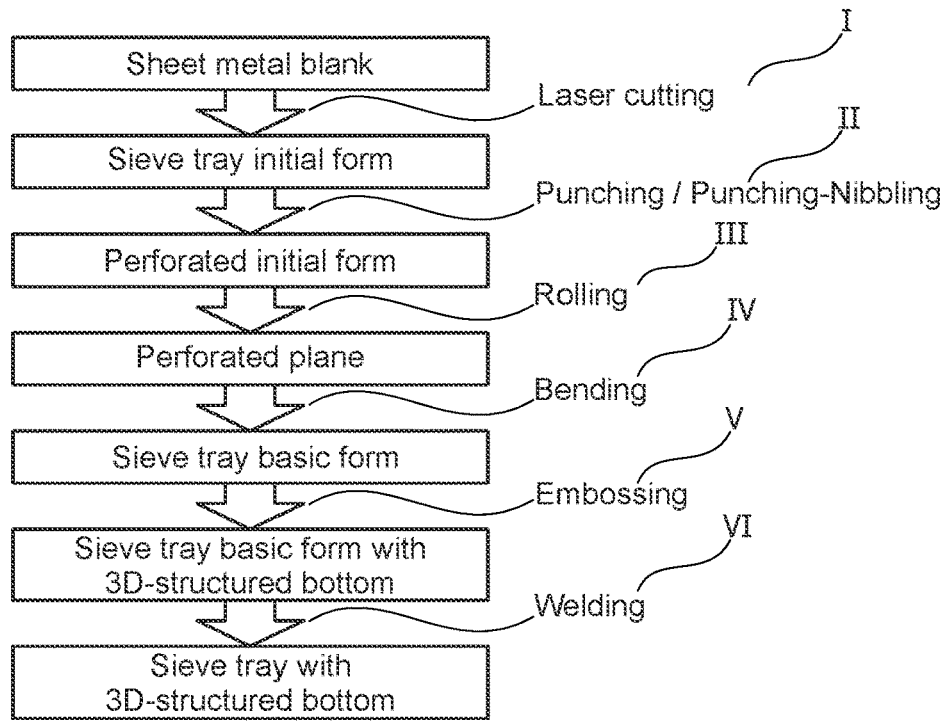
FIG. 6 is another flow chart of the method for manufacturing the stackable sieve tray.

FIG. 6 chronologically shows a second possibility of a process sequence. Hereby, laser cutting I, punching II (also punching-nibbling, if the part to be punched is only partially punched and partially broken), rolling III, bending IV, embossing V and welding VI take place chronologically one after the other.

Figure 7:
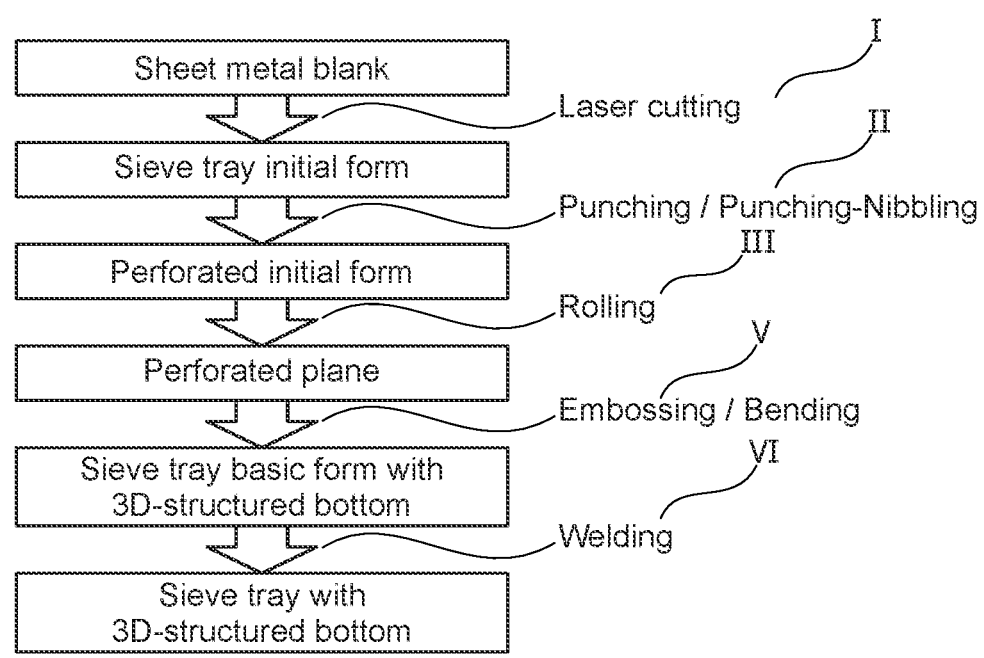
FIG. 7 is yet another flow chart of the method for manufacturing the stackable sieve tray.

A third possibility of a process sequence for the manufacturing of the sieve tray 1 is shown chronologically in FIG. 7. Here, laser cutting I, punching II (also punching-nibbling, if the part to be punched is only partially punched and partially broken), rolling III, an embossing and folding step V and welding VI take place chronologically one after the other.

For manufacturing the sieve tray 1, a rectangular sheet metal blank of any shape and a material thickness of around 0.5 mm to 2 mm, preferably around 1.5 mm, is cut along a cutting contour during laser cutting I, resulting in a sieve tray initial form. After a punching or punching-nibbling step II, there is a perforated initial form with the punched through-holes 10. After cutting I and punching II, the sheet metal in practice has certain residual stresses which lead to a deformation of the initial form. Consequently, rolling III must now be carried out, which rolls/smooths the sheet to obtain a perforated plane.

During embossing V, which produces the desired three-dimensional structure in the manner of an imitation mesh, the circumferential indentation 13 is formed.

After bending IV, a sieve tray shape is obtained, which is finally defined by welding VI, i.e. after bending the sieve tray side walls 4, 6 are welded.

As can be seen in FIGS. 5 to 7, the process sequences of the various manufacturing options differ in the chronological sequence of the individual process steps, in particular bending IV and embossing V. According to the first and second options, embossing V can be carried out before and after bending IV, respectively. Alternatively, embossing V and bending can also be carried out in a single processing step (cf. FIG. 7).

The invention claimed is:

1. A sieve tray for holding medical products, the sieve tray comprising:
a sieve tray bottom;
sieve tray sidewalls arranged on the sieve tray bottom and extending upwards from the sieve tray bottom;
at least one grip handle rotatably articulated to one of the sieve tray sidewalls of the sieve tray; and
a sieve tray lid closing the sieve tray,
the sieve tray defining a first indentation or recess surrounding the sieve tray bottom,
the sieve tray bottom comprising a bottom projection,
said bottom projection and first indentation or recess being configured for fixing the sieve tray and an identically configured sieve tray in a stacked state in which the sieve tray is fixed against lateral displacement relative to the identically configured sieve tray in a length direction and a width direction, with the bottom projection of the sieve tray fit within the sieve tray sidewalls of the identically configured sieve tray,
the sieve tray lid comprising a circumferential rim that surrounds a second indentation or recess intermitted in a region of the grip handle,
the second indentation or recess of the sieve tray lid configured to receive the bottom projection of the identically configured sieve tray, with the bottom projection of the identically configured sieve tray fit within the circumferential rim to fix the sieve tray to the identically configured sieve tray in the stacked state,
wherein the sieve tray lid is recessed downwards in the region of the grip handle and forms a grip handle-receiving portion, so that in a folded position, the grip handle is flush with a surface of the sieve tray lid.

2. The sieve tray according to claim 1, wherein a width of the first indentation or recess of the sieve tray corresponds to a thickness of one of the sieve tray sidewalls of the sieve tray.

3. The sieve tray according to claim 1, wherein the circumferential rim is forms an arc shape that fits over the sieve tray sidewalls when the sieve tray lid is placed on the sieve tray.

4. The sieve tray according to claim 1, wherein a grip handle depression is formed centrally on the grip handle-receiving portion which is recessed downwards in the sieve tray lid.

\* \* \* \* \*